(12) United States Patent
Chandramohan et al.

(10) Patent No.: US 6,265,347 B1
(45) Date of Patent: Jul. 24, 2001

(54) ENHANCED BIOHERBICIDAL CONTROL OF WEEDS USING MULTIPLE PATHOGENS

(75) Inventors: Sankaranarayanaiyer Chandramohan; Raghavan Charudattan, both of Gainesville, FL (US)

(73) Assignee: University of Florida, Gainesville, FL (US)

(*) Notice: Subject to any disclaimer, the term of this patent is extended or adjusted under 35 U.S.C. 154(b) by 0 days.

(21) Appl. No.: 09/272,727

(22) Filed: Mar. 22, 1999

(51) Int. Cl.[7] ............... A01N 63/04; C12N 1/14
(52) U.S. Cl. ............................................. 504/117
(58) Field of Search ...................... 504/117; 435/254.1

(56) References Cited

U.S. PATENT DOCUMENTS

| | | | |
|---|---|---|---|
| 3,849,104 | 11/1974 | Daniel et al. | 71/65 |
| 3,999,973 | 12/1976 | Templeton | 71/79 |
| 4,162,912 | 7/1979 | Charudattan | 71/79 |
| 4,419,120 | * 12/1983 | Walker | 71/79 |
| 4,626,271 | 12/1986 | Gleason | 71/66 |
| 4,775,405 | * 10/1988 | Caulder et al. | 71/79 |
| 4,915,726 | 4/1990 | Bewick et al. | 71/79 |
| 5,212,086 | * 5/1993 | Watson et al. | 504/117 |
| 5,256,627 | 10/1993 | Bewick | 504/117 |
| 5,952,264 | * 9/1999 | Walker et al. | 504/117 |

OTHER PUBLICATIONS

Hoagland, Robert E. "Chemical Interactions with Bioherbicides to Improve Efficacy". Weed Technology. 10:651–674, 1996.*

Strobel, Gary A. "Biological Control of Weeds". Scientific American. pp. 72–78, Jul. 1991.*

* cited by examiner

*Primary Examiner*—S. Mark Clardy
(74) *Attorney, Agent, or Firm*—Saliwanchik, Lloyd & Saliwanchik

(57) ABSTRACT

The subject invention concerns the use of a mixture of fungal pathogens to control the growth of target weed species. Also, the invention concerns three novel fungal pathogens which, in mixture, can be used to control the growth of grassy weeds.

9 Claims, No Drawings

ENHANCED BIOHERBICIDAL CONTROL OF WEEDS USING MULTIPLE PATHOGENS

BACKGROUND OF THE INVENTION

Weeds are a tremendous problem for farmers and growers throughout the world. It has been estimated that about 41% of the cost of plant protection is for the control of weeds. Herbicides are applied to more acres than fungicides and insecticides combined. Weeds act as alternate hosts for insects, fungi, bacteria, and viruses. They affect man, not only by competing with crop plants, but by poisoning range animals, interfering with right-of-ways and roadways, decreasing forest production, and marring landscapes.

Weeds compete with crops for moisture, light, and nutrients and can inhibit crop growth and reduce yields. Competition can be particularly detrimental in tree crops when young trees are being established. In citrus and other tree crops the most problematic weeds are some annual and perennial grass weeds, which are also among the world's worst weeds in many crops worldwide. Some notable examples are: large crabgrass (*Digitaria sanguinalis* [L.] Scop.), crowfootgrass (*Dactyloctenium aegyptium* [L.] Willd.), johnsongrass (*Sorghum halepense* [L.] Pers.), bermudagrass (*Cynodon dactylon* [L.] Pers.), guineagrass (*Panicum maximum* Jacq.), southern sandbur (*Cenchrus echinatus* L.), Texas panicum (*Panicum texanum* Buckl.), and yellow foxtail (*Setaria glauca* [L.] Beauv.).

The use of chemical pesticides in agriculture is currently a major concern in the U.S. Because herbicides are so widely used in agriculture, and because they are often applied directly to the soil, the potential for their movement into groundwater by leaching is perhaps greater than any other pesticide. Other inadequacies of chemical controls include lack of residual control, injury to non-target organisms, undesirable residues in harvested products, and carryover in subsequent crops.

Therefore, the use of bioherbicides is becoming an increasingly important alternative to chemical herbicides. This importance is exemplified by several patents which have been issued for bioherbicides and their use. Some of these patents, by way of illustration, are as follows: U.S. Pat. No. 3,849,104 (control of northern jointvetch with *Colletotrichum gloeosporioides* Penz. *aeschynomene*); U.S. Pat. No. 3,999,973 (control of prickly sida [teaweed] and other weeds with *Colletotrichum malvarum*); U.S. Pat. No. 4,162,912 (control of milkweed vine with *Araujia mosaic* virus); U.S. Pat. No. 4,626,271 (cyanobacterin herbicide); U.S. Pat. No. 4,915,726 (biological control of dodder); U.S. Pat. No. 5,256,627 (control of nutsedge using *Curvularia* and *Fusarium* fungi).

The bioherbicide technology involves mass production, formulation, and inundative application of highly virulent, host-specific plant pathogenic microorganisms at a time conducive for disease development on a population of weeds. This technology has wide commercial applications in weed management. The major challenges to the bioherbicide technology are host-specificity (which typically limits use to one weed per pathogen) and inadequate weed control.

BRIEF SUMMARY OF THE INVENTION

The subject invention concerns materials and methods useful in weed control. More specifically, the subject invention concerns the use of a combination of fungal pathogen isolates to provide enhanced control of multiple weed species. In a specific embodiment, the subject invention provides materials useful in the control of pigweed, sicklepod, and showy crotalaria.

In a preferred embodiment specifically exemplified herein, bioherbicidal control of pigweed (*Amaranthus hybridus* L.), sicklepod (*Senna obtusifolia* [L.] Irwin & Barneby), and showy crotalaria (*Crotalaria spectabilis* Roth.) was achieved using a multiple pathogen strategy consisting of four pathogens applied in a single postemergent spray. The pathogens used were *Phomopsis amaranthicola* sp. nov. Rosskopf et al., (PA, pigweed pathogen), Alternaria cassiae Jurair & Khan (AC, major host, sicklepod; alternative host, showy crotalaria), *Colletotrichum dematium* (Pers.ex. Fr.) Grove f.sp crotalariae and *Fusarium udum* Butler f.sp. crotalariae (Kulkarni) Subramanian (CD and FU: showy crotalaria pathogens). The mixture of these pathogens was able to control all three weed species.

The practice of the subject invention typically involves the use of a composition comprising spores from the above fungal pathogens in association with an agricultural carrier wherein the spores are in a concentration of from about $1 \times 10^4$ spores/ml of carrier to about $1 \times 10^9$ spores/ml of carrier. The concentrated spore formulation can be adapted for distribution such that the spores germinate and infect target weeds.

In a further embodiment, the subject invention discloses the fungal pathogens *Drechslera gigantea, Exserohilum rostratum,* and *Exserohilum longirostratum.* These fungal pathogens can be applied alone or in a mixture to control target grass weeds. Also, compositions comprising spores from these novel fungal pathogens can be used as described herein.

The possibility of controlling several weeds, especially grasses, by a mixture of multiple pathogens, each of which is effective against some but not all hosts, is a novel approach that has not been previously demonstrated with bioherbicides. So far, the emphasis has been on the use of a single, host-specific pathogen to control a single weed. In accordance with the subject invention it is not only possible to control the specific weed hosts of individual pathogens, but also to increase the spectrum of weeds controlled by using the mixture. Such broad-spectrum activity, resulting from advantageous interaction among the pathogens, is a key aspect of this approach. Use of formulations that promote and augment the efficacy of the pathogens, such as an emulsion or other carrier, is another aspect of the subject invention.

DETAILED DISCLOSURE OF THE INVENTION

The subject invention provides a method for controlling multiple weeds using a mixture of fungal plant pathogens. The materials and methods of the subject invention can be used to enhance the efficacy of bioherbicides by increasing the spectrum of weeds controlled and the level of control (i.e., broad-spectrum control and high level of efficacy).

In a preferred embodiment, the compositions of the subject invention comprise three or more fungal isolates. Advantageously, the composition has activity against multiple weeds.

The fungal isolates can be combined according to the subject invention and applied to target weeds. Generally, the application is done by use of the spore form of the fungal pathogen. The fungi of the subject invention can be grown on solid or in liquid media. Solid media that can be used include water agar, potato dextrose agar, V-8 agar, and string bean agar (strained extract of macerated string beans solidified in agar). Spores can be produced on solid V-8 medium exposed to fluorescent light. Specifically, solid media can be, for example, water agar, potato dextrose agar (Difco), lima bean agar (Difco), corn meal agar (Difco), potato-carrot agar (Tuite 19), or Desmodium agar (blend 10 g Desmodium plant parts or plant extracts in 1000 ml water and solidify with 20 g agar).

For large scale production in fermentation tanks, a liquid medium is typically used, for example:

TABLE 1

Formula I: - Modified Richard's Solution - V-8*

| Sucrose | 50 g |
| Potassium nitrate | 10 g |
| Potassium phosphate, monobasic | 5.0 g |
| Magnesium sulfate · 7H$_2$O | 2.50 g |
| Ferric chloride | 0.02 g |
| V-8 juice | 15 ml |
| Distilled water to make | 1000 ml |

*Trademark, The Campbell Soup Company for mixed vegetable juices.

Formula II: Modified Richard's Solution-Distillers Solubles. Same as Formula I above but substitute 15 g Distillers solubles for V-8 juice.

Formula III: Modified Richard's Solution-Brewersyeast. Same as Formula I above but substitute 15 g brewers yeast for V-8 juice.

Formula IV: Modified Richard's Solution-Torula Yeast. Same as Formula I above but substitute 16 g torula yeast for V-8 juice.

Formula V: Oatmeal solution-4%+2% sugar. 40 g oatmeal; 20 g sucrose; 1000 ml distilled water.

The preparation of spores is commenced in preseed liter flasks containing about 300 ml of liquid medium which have been inoculated with spores. The medium is incubated for 1–3 days with agitation at a temperature of about 26° C. to about 30° C.

The preseed is then transferred aseptically to 20 liter seed tanks with additional sterile media. The tanks are provided with sterile air and agitation. The cycle is continued at a temperature of about 26° C. to about 30° C. for 1 to 3 days.

Larger fermentors (250 liter) are aseptically inoculated with the seed tanks (entire contents), described above. Additional sterile medium, as used above, is added and the pH adjusted to about 6.0. The fermentor is supplied with sterile air and agitation, and is maintained at a temperature of about 26° C. to about 30° C. for 1 to 3 days. The fermentor is then harvested by filtering the contents to remove insoluble solids and mycelia growth. The filtered beer is then centrifuged, the supernatant is discarded, and the remaining spore concentrate is collected, placed in plastic bags, and stored in ice. The concentrate so stored maintains an 80% germination rate for up to 21 days.

The spore concentrate is mixed with an agriculturally acceptable diluent or carrier for application to the undesired host vegetation or a situs. By the term "situs" is meant those areas infested with the undesired vegetation or potential infestation sites.

The preferred carrier is water, and the spore concentrate is dispersed to make a concentration of from about $1\times10^4$ to about $1\times10^9$ spores/ml. The formulation is then sprayed on the undesired vegetation or situs by conventional spraying equipment in an amount of from about 50 to 500 liters per hectare.

Some of the fungal isolates of the invention are well-known and readily available to the public. These known fungal isolates include *Phomopsis amaranthicola* (ATCC 74226), *Alternaria cassiae* (ATCC 46687), *Colletotrichum dematium* f.sp. crotalariae (PTA-220) and *Fusarium udum* f.sp. crotalariae (PTA-216).

Other fungal pathogens of the invention are novel. These novel isolates are *Drechslera gigantea, Exserohilum rostratum,* and *Exserohilum longirostratum.* They will be deposited in the permanent collection of the American Type Culture Collection (ATCC), 10801 University Boulevard, Manassas, Va. 20110-2209 USA on Jun. 11, 1999. The culture repository numbers of these isolates are as follows:

| Fungal Pathogen | Culture Deposit No. |
|---|---|
| *Drechslera gigantea* | PTA-219 |
| *Exserohilum rostratum* | PTA-218 |
| *Exserohilum longirostratum* | PTA-217 -- |

Cultures which have been deposited for the purposes of this patent application were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

In one embodiment of the subject invention, the fungal isolate mixtures described herein can be used as a grass edger around homes, gardens, and businesses. For example, the compositions may be used to edge around driveways, trees, shrubs, decorative rocks and structures. In this context, "structures" refers to any man-made object including buildings, walls, and walkways. The specificity and efficacy of these compositions make them highly advantageous for this purpose.

Following are examples which illustrate procedures for practicing the invention. These examples should not be construed as limiting. All percentages are by weight and all solvent mixture proportions are by volume unless otherwise noted.

EXAMPLE 1

Evaluation of "Multiple-Pathogen Strategy" for Bioherbicidal Control of Several Weeds Bioherbicidal control of pigweed (*Amaranthus hybridus*), sicklepod (*Senna obtusifolia*), and showy crotalaria (*Crotalaria spectabilis*) was tested using a multiple-pathogen strategy consisting of four pathogens applied in a single, postemergent spray. The pathogens tested were *Phomopsis amaranthicola* (PA: pigweed pathogen), *Alternaria cassiae* (AC, major host, sicklepod; alternative host, showy crotalaria), *Colletotrichum dematium* f.sp crotalariae and *Fusarium udum* f.sp. crotalariae (CD and FU: showy crotalaria pathogens). A spore suspension of each pathogen alone ($10^6$ per ml) and a cocktail of the four pathogens (1:1:1:1 by volume) were tested on the weed seedlings (six of each weed species per pot, 3 replicates) that were grown together in pots. The inoculum suspensions as well as the control (water only) were amended with 0.5% Metamucil®. The seedlings were sprayed to runoff, given 12 hours of dew at 28° C., and held in a greenhouse. At 1 week after inoculation, AC completely controlled sicklepod and showy crotalaria (100% kill). CD alone completely controlled showy crotalaria in 1 week, and PA completely controlled pigweed at 4 weeks after inoculation. Showy crotalaria inoculated with FU alone, a root-infecting pathogen, did not have any disease incidence. The mixture of all four pathogens controlled all three weed species completely 4 weeks after inoculation (Table 2).

TABLE 2

Bioherbicidal efficacy of multiple-pathogen inoculation on three selected weeds*

| | Pathogen | | | | |
|---|---|---|---|---|---|
| Weed | AC | CD | PA | FU | Mixture (1:1:1:1 v/v) |
| Sicklepod | 100 | 0 | 0 | 0 | 100 |
| Showy crotalaria | 100 | 100 | 0 | 0 | 100 |
| Pigweed | 0 | 0 | 100 | 0 | 100 |

*Disease severity at 4 wk after inoculation = percentage of completely diseased plants compared to uninoculated control. Experimental conditions: completely randomized design, three replicates, six plants per pot. Inoculum level: $10^6$ spores per ml, 12 h dew, 28° C., host-age: 6-leaf stage. AC = *Alternaria cassiae*; CD = *Colletotrichum dematium* f.sp. crotalariae; PA = *Phomopsis amaranthicola*; and FU = *Fusarium udum* f.sp. crotalariae.

Thus, several weeds can be controlled simultaneously with different fungi without loss of efficacy.

EXAMPLE 2

Evaluation of Host-range and Bioherbicidal Efficacy of a Pathogen Mixture to Control Grassy Weeds The multiple-pathogen strategy was also tested using three fungi isolated in Florida, namely, one species of Drechslera and two species of Exserohilum. In greenhouse trials, these pathogens controlled the following eight grasses: bermudagrass (*Cynodon dactylon*), large crabgrass (*Digitaria sanguinalis*), crowfootgrass (*Dactyloctenium aegyptium*), guineagrass (*Panicum maximum*), johnsongrass (*Sorghum halepense*), southern sandbur (*Cenchrus echinatus*), Texas panicum (*Panicum texanum*), and yellow foxtail (*Setaria glauca*).

The seedlings of different ages (1 to 4 weeks after emergence [WAE]) were inoculated with spore suspensions of each pathogen containing $10^5$ spores per ml. A mixture of the three pathogens (1:1:1 by vol) was also tested. The inoculum suspensions as well as the control (water only) were amended with 0.5% Metamucil®. The seedlings were sprayed to runoff, given 12 hours of dew at 28° C., and held in a greenhouse. At $10^5$ spores per ml, young seedlings (1 WAE) were highly susceptible (Table 3), and at $2\times10^5$ spores per ml, even older seedlings (4 WAE) were completely diseased (Table 4).

TABLE 3

Disease severity, 2 wk after inoculation*

| | Age of Host (Wk) | Fungal Pathogen | | | |
|---|---|---|---|---|---|
| Weed | | Drechsle gigantea | Exserohilu longirostratum | Exserohilum rostratum | Mix (1:1:1 v/v) |
| Large Crabgrass | 1 | 13.3 | 0 | 6.6 | 13.3 |
| Guineagrass (Broadleaf) | 1 | 100 | 66.7 | 6.6 | 93.3 |
| Johnsongrass | 1 | 58.3 | 8.3 | 0 | 50 |
| Southern sandbur | 1 | 66.7 | 0 | 0 | 13.3 |
| Crowfootgrass | 1 | 100 | 100 | 0 | 86.6 |
| Yellow foxtail | 1 | 33.3 | 8.3 | 0 | 33.3 |

*Percentage of completely diseased plants, four to five plants per pot, 3 replicates. Experimental conditions: 12 h dew, 28° C., 1 × $10^5$ spores per ml, 0.5% Metamucil. Data analyzed by the LS Means test; standard error: 9.68.

TABLE 4

Disease severity, 2 wk after inoculation*

| | Age of Host (Wk) | Fungal Pathogen | | | |
|---|---|---|---|---|---|
| Weed | | Drechslera gigantea | Exserohilum longirostratum | Exserohilum rostratum | Mix (1:1:1 v/v) |
| Bermudagrass | 4 | 50 | 75 | 25 | 75 |
| Large crabgrass | 4 | 90 | 75 | 75 | 88.3 |
| Guineagrass, narrowleaf | 4 | 100 | 100 | 100 | 100 |
| Johnsongrass | 4 | 100 | 100 | 100 | 100 |
| Southern sandbur | 4 | 100 | 100 | 100 | 100 |
| Crowfootgrass | 4 | 100 | 100 | 100 | 100 |
| Texas panicum | 4 | 100 | 100 | 100 | 100 |
| Yellow foxtail | 4 | 100 | 100 | 100 | 100 |

*Percentage of completely diseased leaves per plant compared to control, five plants per pot, 3 replicates. Experimental conditions: 12 h dew, 28° C., 2 × $10^5$ spores per ml, 0.5% Metamucil. Data were analyzed by the LS Means test; standard error 1.28.

In a host-range trial, the crop species tested (at $10^5$ spores per ml), including corn (Asgrow), oats (FL502 and Fulghum), wheat (Triticale, Morey, and FL301), sorghum (TX398, DK104, and DK58) and rye (Greenacres and GrazeMaster) developed less than 1% leaf damage, characterized by resistant reaction, when inoculated with Drechslera sp. None of the crops developed disease when inoculated with Exserohilum spp. or the pathogen mixture (Table 5).

TABLE 5

Disease severity, 2 wk after inoculation*

| Crop | | Age of Host (Wk) | Drechslera gigantea | Exserohilum longiostratum | Exserohilum rostratum | Mix (1:1:1 v/v) |
|---|---|---|---|---|---|---|
| Corn | (Asgrow) | 2 | 1 | 0 | 0 | 0 |
| Wheat | (FL 301) | 2 | 1 | 0 | 0 | 0 |
|  | (Morey) | 2 | 1 | 0 | 0 | 0 |
|  | (Triticale) | 2 | 1 | 0 | 0 | 0 |
| Oat | (Fulghum) | 2 | 1 | 0 | 0 | 0 |
|  | (FL 502) | 2 | 1 | 0 | 0 | 0 |
| Sorghum | (DK 58) | 2 | 1 | 0 | 0 | 0 |
|  | (DK 104) | 2 | 1 | 0 | 0 | 0 |
|  | (TX398) | 2 | 1 | 0 | 0 | 0 |
| Rye | (Graze-Master) | 2 | 1 | 0 | 0 | 0 |
|  | (Green-acres) | 2 | 1 | 0 | 0 | 0 |

*Visual rating compared to control, five plants per pot, 3 replicates. Experimental conditions: 12 h dew, 28° C., $1 \times 10^5$ spores per ml, 0.5% Metamucil.

EXAMPLE 3

Field-testing of the Pathogen Mixture to Control Grassy Weeds in Florida

The pathogens were field-tested in two locations in Florida. At Lake Alfred, 2-wk-old seedlings of seven grasses (large crabgrass, crowfootgrass, johnsongrass, guineagrass, southern sandbur, Texas panicum, and yellow foxtail) were transplanted randomly (25 seedlings/sq.m.plot; factorial RCB) and inoculated, when 4-wk old, with spore suspensions of each pathogen alone or a mixture of the three pathogens (1:1:1 by vol). The fungi were applied as foliar sprays ($5 \times 10^5$ spores per ml) in one of three carriers: water, 0.5% aqueous Metamucil®, or an emulsion. Appropriate controls were included. During the following fourteen weeks two more applications of treatments were made at 2 or 3 weeks after initial spray (WAI). Disease severity (DS; Horsfall-Barratt scale) was recorded weekly, for 4–6 WAI. At 4 WAI, DS in emulsion treatments on the various grasses ranged from 50.88–100% (*Drechslera gigantea*), 78.13–99.6% (*Exserohilum longirostratum*), 43.75–100% (*Exserohilum rostratum*), and 63.38–100% (mix) (Table 6).

It was possible to control these grasses using an emulsion-based inoculum preparation of each pathogen as well as the pathogen mixture. At Fort Pierce, bioherbicidal control of a natural population of guineagrass (*Panicum maximum*) was tested using an experimental design and treatments identical to those of the Lake Alfred study. During the following 10 weeks a second application of all treatments was made at 2 WAI. At 4 WAI, DS in emulsion treatments ranged from 93.75–98.50% (Table 7).

TABLE 7

Effect of inoculation of species of Drechslera and Exserohilum on guineagrass*

| Isolate | Carrier | | |
|---|---|---|---|
|  | W | M | E |
| CB | 1.50 | 4.88 | 98.00 |
| CW | 3.75 | 7.88 | 96.50 |
| JG | 7.25 | 5.63 | 93.75 |
| MIX | 3.00 | 9.13 | 98.50 |

*Disease severity at 4 wk after initial spray, factorial RCB, four replicates. CB = *Drechslera gigantea* (crabgrass isolate); CW = *Exserohilum longirostratum* (crowfootgrass isolate); JG = *Exserohilum rostratum* (johnsongrass isolate); MIX = mixture of three isolates (1:1:1 v/v). W = Water; M = Metamucil; E = Emulsion.

Individual pathogens as well as the mixture of three pathogens were effective. Thus, it was possible to control a natural population of guineagrass using an emulsion-based inoculum preparation.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A composition for agricultural application for controlling target weeds, wherein said composition comprises *Phomopsis amaranthicola*, *Alternaria cassiae*, *Colletotrichum dematium*, and *Fusarium udum*.

2. The composition, according to claim 1, wherein said fungi are in the spore form at a concentration of from about $1 \times 10^4$ spores/ml of carrier to about $1 \times 10^9$ spores/ml of carrier.

3. A method for controlling multiple weed species wherein said method comprises applying to said weeds a mixture of fungal pathogens, wherein said fungal pathogens

TABLE 6

Effect of inoculation of species of Drechslera and Exserohilum on selected grass weeds*

| Isolates | CB | | | CW | | | JG | | | MIX | | |
|---|---|---|---|---|---|---|---|---|---|---|---|---|
| Weed | W | M | E | W | M | E | W | M | E | W | M | E |
| LC | 6.00 | 11.38 | 50.88 | 7.88 | 7.88 | 78.13 | 7.88 | 7.88 | 43.75 | 10.25 | 13.50 | 63.38 |
| CF | 16.13 | 28.00 | 93.13 | 24.83 | 28.00 | 95.38 | 28.00 | 28.00 | 80.38 | 18.50 | 28.00 | 94.30 |
| JG | 28.00 | 39.00 | 93.5 | 32.80 | 43.80 | 85.30 | 32.90 | 50.00 | 92.38 | 28.00 | 35.00 | 91.00 |
| GG | 28.00 | 32.75 | 69.63 | 28.00 | 39.00 | 88.50 | 32.80 | 34.30 | 94.50 | 23.30 | 32.80 | 94.63 |
| TP | 18.50 | 32.80 | 74.38 | 28.00 | 50.00 | 89.67 | 32.80 | 46.13 | 69.50 | 18.50 | 37.50 | 90.00 |
| SS | 23.25 | 28.00 | 93.75 | 28.00 | 37.50 | 95.00 | 23.30 | 32.80 | 95.75 | 15.80 | 32.80 | 95.50 |
| YFT | 32.75 | 37.50 | 100.00 | 39.00 | 50.88 | 99.63 | 28.00 | 39.00 | 100.00 | 28.00 | 48.50 | 100.00 |

*Disease severity at 4 wk after initial spray, factorial RCB, four replicates. CB = *Drechslera gigantea* (crabgrass isolate); CW = *Exserohilum longirostratum* (crowfootgrass isolate); JG = *Exserohilum rostratum* (johnsongrass isolate); MIX = mixture of 3 isolates (1:1:1 v/v). W = Water; M = Metamucil; E = Emulsion. LC = large crabgrass; CF = crowfootgrass; JG = johnsongrass; G G = Guineagrass; TP = Texas panicum; SS = Southern sandbur; YFT = yellow foxtail.

are *Phomopsis amaranthicola, Alternaria cassiae, Colletotrichum dematium*, and *Fusarium udum*, and wherein said mixture of fungal pathogens control the growth of the weed species *Amaranthus hybridus, Senna obtusifolia* and *Crotolaria spectabilis*.

4. A method for controlling target grassy weed species, said method comprising the application of a mixture of fungi to said target grassy weed species or their situs, wherein said fungi are *Drechslera gigantea* having the characteristics of ATCC PTA-219, *Exserohilum rostratum* having the characteristics of ATCC PTA-218, and *Exserohilum longirostratum* having the characteristics of ATCC PTA-217, and wherein said fungi in a mixture control the grassy weed species bermudagrass (*Cynodon dactylon*), large crabgrass (*Digitaria sanguinalis*), crowfootgrass (*Dactyloctenium aegyptium*), guineagrass (*Panicum maximum*), johnsongrass (*Sorghum halepense*), southern sandbur (*Cenchrus echinatus*), Texas panicum (*Panicum texanum*), and yellow foxtail (*Setarla glauca*).

5. The method, according to claim 3, wherein said method is used to edge around desired vegetation or structures.

6. A biologically pure culture of a fungal pathogen selected from the group consisting of *Drechslera gigantea* having the characteristics of ATCC PTA-219, *Exserohilum rostratum* having the characteristics of ATCC PTA-218, and *Exserohilum longirostratum* having the characteristics of ATCC PTA-217.

7. A composition for agricultural application for controlling grassy weeds comprising isolates of the fungi *Drechslera gigantea* having the characteristics of ATCC PTA-219, *Exserohilum rostratum* having the characteristics of ATCC PTA-218, and *Exserohilum longirostratum* having the characteristics of ATCC PTA-217, and wherein said fungi in a mixture can control the growth of the grassy weed species bermudagrass (*Cynodon dactylon*), large crabgrass (*Digitaria sanguinalis*), crowfootgrass (*Dactyloctenium aegyptium*), guineagrass (*Panicum maximum*), johnsongrass (*Sorghum halepense*), southern sandbur (*Cenchrus echinatus*), Texas panicum (*Panicum texanum*), and yellow foxtail (*Setarla glauca*).

8. The composition, according to claim 7, wherein said fungi are in the spore form at a concentration of from about $1 \times 10^4$ spores/ml of carrier to about $1 \times 10^9$ spores/ml of carrier.

9. A method for inhibiting the growth of a grassy weed wherein said method comprises the application of a fungus to said target grassy weed or its situs, wherein said fungus is selected from the group consisting of a *Drechslera gigantea* having the characteristics of ATCC PTA-219, a *Exserohilum rostratum* having the characteristics of ATCC PTA-218, and a *Exserohilum longirostratum* having the characteristics of ATCC PTA-217; and said target grassy weed is selected from the group consisting of *Digitaria sanguinalis, Sorghum halepense*, and *Dactyloctenium aegyptium*.

* * * * *